(12) United States Patent
Einarsson et al.

(10) Patent No.: US 7,704,218 B2
(45) Date of Patent: Apr. 27, 2010

(54) KNEE BRACE

(75) Inventors: Palmi Einarsson, San Juan Capistrano, CA (US); Arni Thor Ingimundarson, Ladera Ranch, CA (US)

(73) Assignee: Ossur, HF, Reykjavik (IS)

( * ) Notice: Subject to any disclaimer, the term of this patent is extended or adjusted under 35 U.S.C. 154(b) by 229 days.

(21) Appl. No.: 11/546,244

(22) Filed: Oct. 12, 2006

(65) Prior Publication Data

US 2007/0083136 A1    Apr. 12, 2007

Related U.S. Application Data (60) Provisional application No. 60/725,306, filed on Oct. 12, 2005.

(51) Int. Cl.
*A61F 5/00* (2006.01)
*A63B 20/002* (2006.01)
*A63B 21/02* (2006.01)
*A63B 21/00* (2006.01)

(52) U.S. Cl. .............................. 602/16; 602/5; 602/12; 602/14; 602/23; 602/26; 128/882; 482/91; 482/121; 482/122; 482/125

(58) Field of Classification Search .............. 602/5–6, 602/12, 16, 24–26, 60–62; 128/882; 482/91, 482/121–122, 125, 135–136
See application file for complete search history.

(56) References Cited

U.S. PATENT DOCUMENTS

| | | | |
|---|---|---|---|
| 161,323 A | 3/1875 | Brown et al. | |
| 183,376 A | 10/1876 | Darrach | |
| 552,143 A | 12/1895 | Rankin | |
| 646,659 A | 4/1900 | Gail | |
| 1,446,230 A | 2/1923 | Welter | |
| 3,304,937 A | 2/1967 | Callender, Jr. | |
| 3,526,222 A | 9/1970 | Dreibelbis | |
| 3,799,159 A | 3/1974 | Scott | |
| 3,831,467 A | 8/1974 | Moore | |
| 3,928,872 A | 12/1975 | Johnson | |

(Continued)

FOREIGN PATENT DOCUMENTS

CH    170152    3/1934

(Continued)

OTHER PUBLICATIONS

U.S. Appl. No. 10/675,324, filed Sep. 29, 2003, Cormier et al.

(Continued)

*Primary Examiner*—Patricia M Bianco
*Assistant Examiner*—Brandon Jackson
(74) *Attorney, Agent, or Firm*—Bacon & Thomas, PLLC (57) ABSTRACT

A knee brace adapted for placement over at least a posterior side of a leg and comprising a first posterior frame member, a second posterior frame member connected to first frame member, and a posterior resilient hinge device located at or near a first end portion of the first frame member. The hinge device is arranged to urge the first and second frame members into a predetermined alignment. The hinge device can be arranged for selectively locking the second frame member at an angle relative to the first frame member, and permitting rotation of the second frame member relative to first frame member within a range of predetermined angles.

16 Claims, 10 Drawing Sheets

U.S. PATENT DOCUMENTS

| | | |
|---|---|---|
| 3,933,154 A | 1/1976 | Cabansag |
| 3,935,858 A | 2/1976 | Harroff |
| 3,958,567 A | 5/1976 | Callender, Jr. |
| 4,041,940 A | 8/1977 | Frankel et al. |
| 4,050,455 A | 9/1977 | Smith |
| 4,090,508 A | 5/1978 | Gaylord, Jr. |
| 4,111,194 A | 9/1978 | Cox et al. |
| 4,130,115 A | 12/1978 | Taylor |
| 4,198,964 A | 4/1980 | Honneffer |
| 4,275,716 A | 6/1981 | Scott, Jr. ............ 128/80 |
| 4,388,920 A | 6/1983 | Hajost et al. ............ 128/80 |
| 4,407,276 A | 10/1983 | Bledsoe |
| 4,408,600 A | 10/1983 | Davis |
| 4,450,832 A | 5/1984 | Waddell |
| 4,489,718 A | 12/1984 | Martin |
| 4,522,199 A | 6/1985 | Waddell et al. |
| 4,776,326 A | 10/1988 | Young et al. |
| 4,796,610 A | 1/1989 | Cromartie |
| 4,844,326 A | 7/1989 | Kashihara et al. |
| 4,848,326 A | 7/1989 | Lonardo |
| 4,981,132 A | 1/1991 | Chong |
| 4,982,732 A | 1/1991 | Morris |
| 5,007,415 A | 4/1991 | Marion |
| 5,088,479 A | 2/1992 | Detoro |
| 5,116,296 A | 5/1992 | Watkins et al. |
| 5,230,700 A | 7/1993 | Humbert et al. |
| 5,261,949 A | 11/1993 | Schilling |
| 5,267,949 A | 12/1993 | De La Torre et al. |
| 5,269,322 A | 12/1993 | Mandel |
| 5,277,698 A | 1/1994 | Taylor |
| 5,385,534 A | 1/1995 | Cassford ............ 602/15 |
| 5,387,185 A | 2/1995 | Johnson, Jr. et al. |
| 5,401,235 A | 3/1995 | Devens |
| 5,456,659 A | 10/1995 | Gildersleeve et al. ........ 602/15 |
| 5,472,409 A * | 12/1995 | Hoy ............ 602/5 |
| 5,486,157 A | 1/1996 | DiBenedetto |
| 5,545,127 A | 8/1996 | DeToro |
| 5,554,104 A | 9/1996 | Grim |
| 5,571,206 A | 11/1996 | Varn |
| 5,593,383 A | 1/1997 | DeToro |
| 5,732,411 A | 3/1998 | Coleman et al. |
| 5,788,658 A | 8/1998 | Islava |
| 5,823,931 A * | 10/1998 | Gilmour ............ 602/24 |
| 5,908,398 A | 6/1999 | DeToro |
| 5,944,679 A | 8/1999 | DeToro |
| D429,816 S | 8/2000 | Rohrs et al. ............ D24/190 |
| 6,302,858 B1 | 10/2001 | DeToro et al. |
| 6,350,246 B1 | 2/2002 | DeToro et al. |
| 6,377,178 B1 | 4/2002 | DeToro et al. |
| 6,383,156 B1 | 5/2002 | Enzerink et al. |
| 6,464,659 B1 | 10/2002 | DeToro et al. |
| 6,471,664 B1 | 10/2002 | Campbell et al. |
| 6,508,281 B1 * | 1/2003 | Wang ............ 144/287 |
| 6,524,110 B1 | 2/2003 | Eastwood |
| 6,540,703 B1 | 4/2003 | Lerman |
| 6,592,539 B1 | 7/2003 | Einarsson et al. |
| 6,719,713 B2 | 4/2004 | Mason |
| 6,746,248 B2 | 6/2004 | Eastwood |
| D496,464 S | 9/2004 | Iglesias et al. |
| 6,821,261 B2 | 11/2004 | Doty et al. |
| 7,011,641 B1 | 3/2006 | DeToro et al. |
| 7,122,016 B1 | 10/2006 | DeToro et al. |
| 7,128,723 B2 | 10/2006 | Doty et al. |
| 2002/0072695 A1 | 6/2002 | Doty et al. |
| 2002/0183672 A1 | 12/2002 | Enzerink et al. |
| 2003/0093018 A1 | 5/2003 | Albrecht et al. |
| 2005/0101895 A1 | 5/2005 | Patel ............ 602/16 |
| 2005/0234374 A1 | 10/2005 | Grim et al. |
| 2006/0058893 A1 | 3/2006 | Clausen et al. ............ 623/53 |
| 2006/0197051 A1 | 9/2006 | Hsu et al. ............ 252/62.52 |
| 2006/0206215 A1 | 9/2006 | Clausen et al. ............ 623/24 |
| 2007/0232972 A1 | 10/2007 | Martinez |

FOREIGN PATENT DOCUMENTS

| | | |
|---|---|---|
| DE | 3245471 A1 | 8/1982 |
| DE | 3520939 | 12/1986 |
| WO | WO 87/06820 | 11/1987 |
| WO | WO 93/15251 | 8/1993 |

OTHER PUBLICATIONS

Celebrating the Introduction of the KMO Knee Management Orthosis, Anatomical Concepts, Inc., Product brochure.

* cited by examiner

KNEE BRACE

This application claims the benefit of priority from U.S. provisional application 60/725,306 filed on Oct. 12, 2005.

FIELD OF THE INVENTION

This application pertains to orthopedic devices, and in particular to knee bracing.

BACKGROUND

Knee braces are used to stabilize the knee by preventing excessive movement of the knee, or to facilitate movement of the knee. Many braces comprise a frame and have hinges located on at least one of the lateral and medial sides of the knee joint. Straps are used to secure the brace to the leg or knee. An injured knee can be fit with an "off the shelf" brace or a custom fit brace, with the selection of the type of brace depending on the size and shape of an individual's leg.

Many knee braces are designed to reduce knee instability following an injury, fatigue or to treat impairment of the knee, particularly if the knee has damaged ligaments. Braces may be recommended for walking, skiing, running, twisting, pivoting, or jumping activities. In addition to providing increased stability to the knee, braces may also decrease the risk of injuring the knee or leg, or provide corrective assistance to the knee.

Braces are apt for protecting knee joints and supplementing knee joints. For example, skiers often experience fatigue in their quadriceps which may lead to knee pain due to overstressed muscles and joints. While many solutions exist for supplementing the knee joint by taking some of the load of the skier off of the knee; these solutions are often cumbersome and inhibit certain movement by the skier when the skier is not engaged in skiing such as when he is riding a ski lift.

Braces designed for assisting individuals having trouble in controlling the muscles in their legs are of particular interest. The need for knee treatment for these individuals is generally the result of a stroke or an accident, or for individuals with spinal cord injuries or birth defects which impair control of the legs and knees. Typically, these individuals require both stability at the knee and some dynamic assistance for moving the knee joint, thereby enabling the individual to walk.

Some drawbacks of known knee braces are that the braces keep the leg straight, and that there is no dynamic response when the knee is bent. By letting the knee bend, injuries of the knee can heal faster, and rehabilitation can occur much quicker. Also, by providing a brace with dynamic response, individuals with leg and knee impairment may use braces to walk in a natural manner, the intention being to allow the wearer both to walk normally and also to carry out physical exercise.

Another drawback to known knee braces is that individuals consider them to be heavy, hot and bulky in size. Many braces are expensive and include complex hinge mechanisms and awkward strap arrangements. It is found that sometimes these braces do not always work or they fail to treat the knee as intended, either by simply failing to stabilize the knee or not sufficiently securing to the leg. Moreover, some braces continually restrain movement by the wearer when the brace is worn and fail to provide selective corrective action when such correction is required only intermittently.

SUMMARY

Embodiments of the present invention are directed to a knee brace that serve to stabilize the knee and provide dynamic response when the knee is rotated. The embodiments are lightweight, have a slim profile with means for ventilating the brace, and function in a simple manner. Moreover, certain embodiments provide selective corrective action when such correction is required only intermittently.

In accordance with one embodiment, a knee brace is intended to be mounted on the posterior side of a knee. The brace comprises a lower frame member having branching first and second arms, and a hinge located near a first end portion on the posterior side of the knee. The brace also includes an upper frame member having a first end portion that is pivotably joined to the first end portion of the lower frame member, and a second end portion having first and second arms. The first and second arms of the lower and upper frame members each define a curved portion that is intended wrap around lateral and medial sides of a leg so as to extend to the anterior side of the leg. Suitable padding features are secured to a second side of the lower and upper frame members that faces the intended leg.

According to a variation of the hinge, the hinge is formed from the lower frame member, and includes a plurality of raised undulating portions that extend outwardly from the brace and away from the posterior side of an intended leg.

According to a variation of the padding feature, the padding feature comprises material that provides cushioning to the leg. In another variation, the padding feature is coated with a silicone material that has frictional features that prevent rotation of the first and second members when secured to a leg. The padding may be ventilated and the silicone coating may comprise a plurality of apertures facilitating the ventilation.

According to a variation of the first and second members, the lower and upper frame members are single-body entities. In another variation, the lower and upper frame members have a ventilated structure. The ventilated structure may comprise a plurality of apertures, elongate openings, or any other suitable shape that are formed from the body of the lower and upper frame members. In addition, the padding feature may have a ventilation feature that corresponds with the ventilated structure of the lower and upper frame members so as to facilitate breathability of the knee brace.

The lower and upper frame members may be pivotably adjustable relative to one another, thereby providing varus or valgus adjustment to the knee brace. A dial or other suitable mechanism may be used to permit easy adjustment and fastening of the lower and upper frame members relative to one another.

The lower and upper frame members may be constructed from a variety and combination of such variety of materials, including carbon fiber composites, glass fibers, polypropylene, and other suitable materials. The frame members may be substantially rigid, or alternatively flexible yet structurally strong so as to flex about the leg of the wearer and redistribute the weight on the knee to the legs of the wearer.

In accordance with another embodiment, a knee brace is provided which includes a hinge device arranged for selectively locking a second frame member at an angle relative to a first frame member, and permitting rotation of the second frame member relative to first frame member within a range of predetermined angles.

This embodiment includes the first posterior frame member having front and rear surfaces, and including a first end portion, a central portion connecting to the first end portion, and a second end portion having at least one arm branching from the central portion and about a central longitudinal axis. The second posterior frame member has front and rear surfaces, and includes a first end portion joined to the first end portion of the first member, a central portion connecting to the first end portion, and a second end portion having at least one arm branching from the central portion.

The hinge device connects the first and second frame members relative to one another, and is arranged for selectively locking the second frame member at an angle relative to the first frame member, The hinge device permits rotation of the second frame member relative to the first frame member within a predetermined range of angles.

According to one variation, the hinge device includes a resilient cantilever spring secured to the first frame member, and lower and upper hinge elements connected to one another via a joint. The upper hinge element is selectively engageable with the cantilever spring. The locking of the hinge device is obtained by a locking mechanism supported by the upper hinge element. The locking mechanism is configured to selectively secure the cantilever spring relative to the upper hinge element thereby positioning the upper frame member relative to the lower frame member at a predetermined angle.

The hinge device may include lower and upper brackets that connect to the first and second frame members respectively, and form channels therewith for receiving end portions of the cantilever spring and the lower and upper hinge elements. The lower and upper hinge elements may include elongate grooves defined along edges thereof for receiving ribs defined along interior surfaces of the lower and upper brackets thereby permitting the lower and upper hinge elements to slide linearly relative to the lower and upper brackets.

The knee brace may include protrusions extending from the posterior or rear surface thereof. The protrusions extend through corresponding elongate slots defined by the cantilever spring, and the lower and upper hinge elements. Moreover, the elongate slots of the lower and upper hinge elements may include at least one spring element arranged to restrict sliding of the frame member protrusions within the elongate slots.

With the arrangement of the hinge device, the second frame member is arranged to be locked relative to the first frame member within the predetermined range of 5° to 30°. The hinge device permits rotation of the second frame member relative to the first frame member within the predetermined range. It follows that when hinge device is not locked, the locking mechanism is released from the cantilever spring, and the upper frame member is able to move freely relative to the lower frame member thereby permitting the wearer a freedom of motion of approximately 0°-140°.

BRIEF DESCRIPTION OF THE DRAWINGS

These and other features, aspects, and advantages of the present invention will become better understood with regard to the following description, appended claims, and accompanying drawings where:

DETAILED DESCRIPTION OF VARIOUS EMBODIMENTS

A. Overview

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Environment and Context of Embodiments

Numerous embodiments of the invention are provided which are designed to stabilize a knee joint that has been weakened by injury or other infirmities. Embodiments of the invention are particularly adapted for a human knee joint, and may be dimensioned to accommodate different types, shapes and sizes of human joints and appendages.

In particular, the knee brace embodiments described herein are configured to support and stabilize a knee joint, and to provide energy return to the knee so as to assist the return of the leg and knee to a straight configuration when the knee is bent. A resilient hinge device is generally provided which corresponds to the posterior of the knee so that it is flexed at generally the same location at which the knee is bent. Due to the resiliency of the hinge, the leg is urged into a generally straight configuration when the leg is bent.

Lower and upper frame members are provided for leg portions located lower and upper the knee, and are connected to one another with the hinge. The lower and upper frame members position the hinge relative to the knee, and further distribute loads placed on the knee to the upper and lower leg portions.

The embodiments described herein provide different knee brace constructions to support and stabilize a knee joint with a posterior hinge device. These embodiments provide features which may be selectively used to replace corresponding features in any one of the other embodiments or variations described herein.

For explanatory purposes, the embodiments described herein are divided into sections which are denoted by general anatomical terms for the human body. These terms include dividing the knee brace into anterior and posterior sections by an anterior-posterior plane. The anterior-posterior plane generally corresponds to the coronal or frontal plane of a human leg. Each of the anterior and posterior sections is further divided about the center of the leg by a proximal-distal plane and a lateral-medial plane.

The anatomical terms described herein are not intended to detract from the normal understanding of such terms as readily understood by one of ordinary skill in the art of orthopedics.

Any of the embodiments described herein may be adapted to include any of the components, such as straps, tightening devices and buckles, described in co-pending U.S. application Ser. No. 11/312,514 filed on Dec. 21, 2005 and incorporated herein by reference. Moreover, any of the components described herein may be constructed in the manner or from the materials described in co-pending U.S. application Ser. No. 11/312,514.

C. Various Embodiments of the Knee Brace

Figure 1:
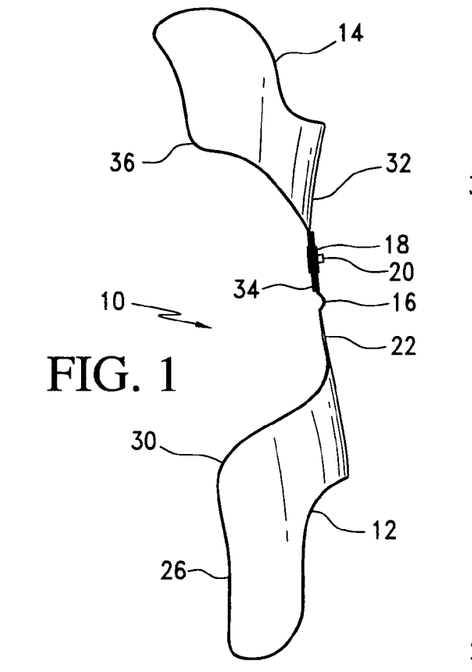
FIG. 1 is side elevational view of an embodiment of a knee brace having a posterior hinge device.
Figure 2:
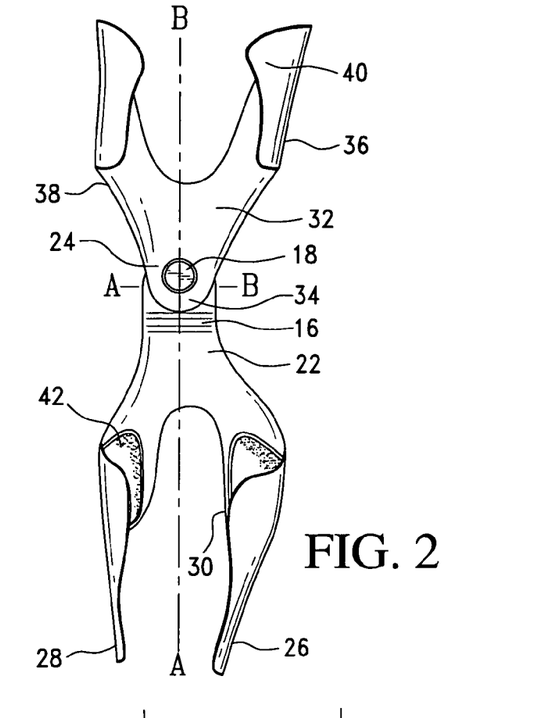
FIG. 2 is a front elevational view of the embodiment of FIG. 1.
Figure 3:
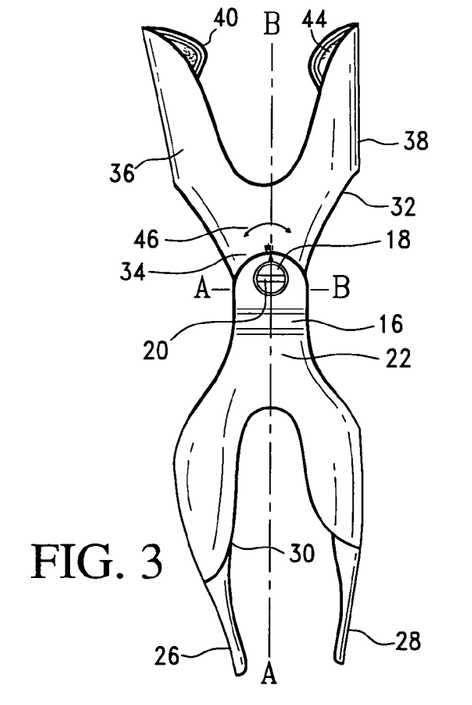
FIG. 3 is a rear elevational view of the embodiment of FIG. 1.

One embodiment of the knee brace 10 is shown in FIGS. 1-3. The knee brace 10 is configured for positioning on the posterior side of the leg, and has upper and lower frame members 12, 14. The first or lower frame member 12 defines front or anterior, and rear or posterior surfaces, and includes a first end portion 24, a central portion 22, and a second end portion defined by first and second arms 26, 28 branching from the central portion 22.

The lower frame member 12 includes a hinge 16 that is located near the first end portion 24. The hinge 16 is formed from the lower frame member 12 and has a profile that is defined as an undulation or a peak that extends outwardly from the first member 12 and away from the posterior side of an intended leg. While only one undulation is shown in the exemplary views of FIGS. 1-3, it will be understood that the hinge 16 may be defined by a plurality of undulations along the central portion 22.

The second or upper frame member 14 has front and rear surfaces, and includes a first end portion 34 that is joined to the first end portion 24 of the first member 12, a central portion 32, and a second end portion defined by first and second arms 38, 40 extending from the branch from the central portion 32.

The lower and upper frame members 12, 14 are connected at a joint 18 that permits the lower and upper frame members to be pivotably adjustable relative to one another. A suitable adjustment mechanism 20 is provided which permits the adjustment of the lower and upper frame members relative to one another so as to provide varus or valgus adjustment for an intended wearer of the brace 10. The adjustment mechanism may be any type of device which permits selective securing of the lower and upper frame members relative to one another.

The first and second arms of both the lower and upper frame members 12, 14 are provided to correspond to medial and lateral sides of the leg depending on which side of the leg the knee brace 10 is fitted for.

The lower frame member 12 and the upper frame member 14 each define a longitudinal, central axis A-A, B-B, respectively. Each of the first and second arms 26, 28 of the lower frame member 12 has a curved portion 30 that extends about the axis A-A and is intended to wrap about the leg so as to extend from the posterior side to at least a portion of the anterior side of an intended leg. The first and second arms 26, 28 may have greater curvature at a location closer to the first end portion 24 than at the opposed second end of the lower frame member 12. The first and second arms 36, 38 of the upper frame member 14 also each has a curved portion 40 that extends about the axis B-B to wrap about the leg so as to extend from the posterior side to at least a portion of the anterior side of an intended leg.

While the axes A-A and B-B are shown as generally in alignment with one another, the lower and upper frame members 12, 14 may be adjusted relative to one another so that the axes A-A and B-B are not aligned. This would be desirable is there is need to provide varus or valgus adjustment for the intended wearer of the brace. This of course can be achieved by using the adjustment mechanism 20 that is used to secure the lower and upper frame members 12, 14 to one another. Suitable indicia 46 is provided on the rear surface of one of the lower and upper frame members 12, 14 to indicate the orientation in which the frame members should be adjusted to obtain varus or valgus adjustment.

Both the lower and upper frame members 12, 14 include a padding feature 42, 44 that is located on the second surface of the lower and upper frame members 12, 14 along regions of their respective first and second arms. The padding feature 42, 44 may comprise any one or combination of materials such as foam, textile, or any other suitable padding material known to those skilled in the art such as those used for spacers in U.S. application Ser. No. 11/312,514.

The padding feature 42, 44 may include a frictional feature that maintains the lower and upper frame members 12, 14 from rotating or shifting about a leg. The frictional feature, according to one variation, is an apertured silicone coating that provides ventilation, as taught in U.S. application Ser. No. 11/312,514. Other suitable frictional features may be employed that prevent the lower and upper frame members from rotating or shifting about a leg.

Figure 4:
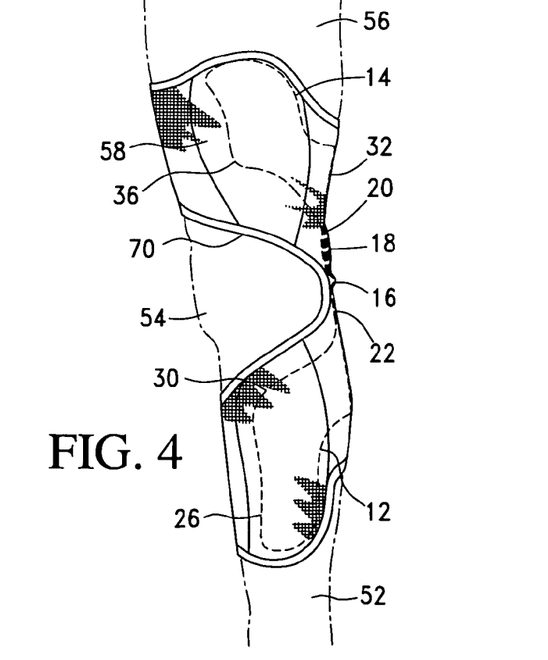
FIG. 4 is side schematic elevational view of the embodiment of FIG. 1 having a sleeve placed thereover.

FIG. 4 exemplifies the brace 10 located on a leg having a lower leg portion 52, knee portion 54 and upper leg portion 56. The brace is illustrated as being located generally on the posterior side of the knee portion 54, whereat the hinge 16 extends outwardly from posterior side of the knee portion 54. The lower frame member 12 is configured for securing to the lower leg portion 52 and the upper frame member 14 is configured for securing to upper leg portion 56.

According to this variation, a sleeve 58 is provided which covers the first surface of the brace 10. The sleeve 58 includes a knee portion 70 that is defined as an opening on the anterior side of the knee portion 54 of the leg. The first surfaces of the lower and upper frame members 12, 14 may be secured to an inside surface of the sleeve 58, or in the alternative, the sleeve 58 may include pockets wherein portions of the brace may be inserted therein. Other means may be provided to secure the brace to the inside surface of the sleeve including hook and loop fasteners, stitching, adhesives, or snap fasteners. The sleeve 58 may be constructed in a similar manner as in the sleeve embodiments taught by U.S. application Ser. No. 11/312,514.

Figure 5:
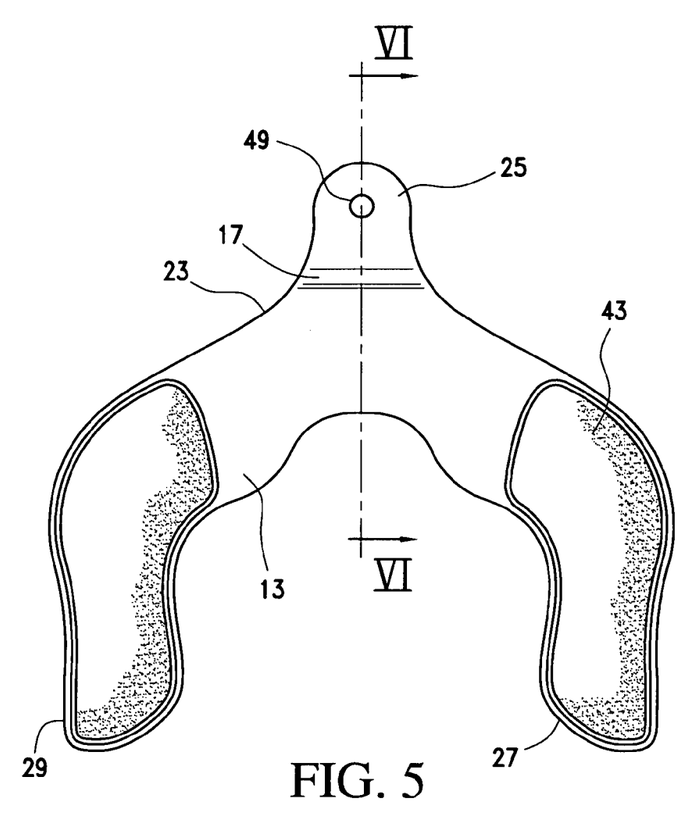
FIG. 5 is front elevational view of a precut and non-customized lower frame member of the embodiment of FIG. 1.
Figure 6:
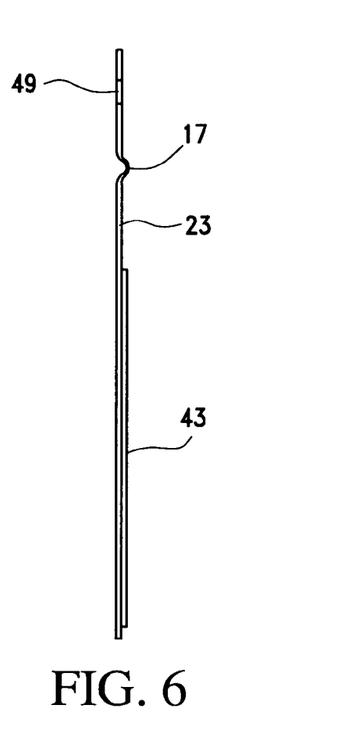
FIG. 6 is a sectional view taken from FIG. 5.
Figure 7:
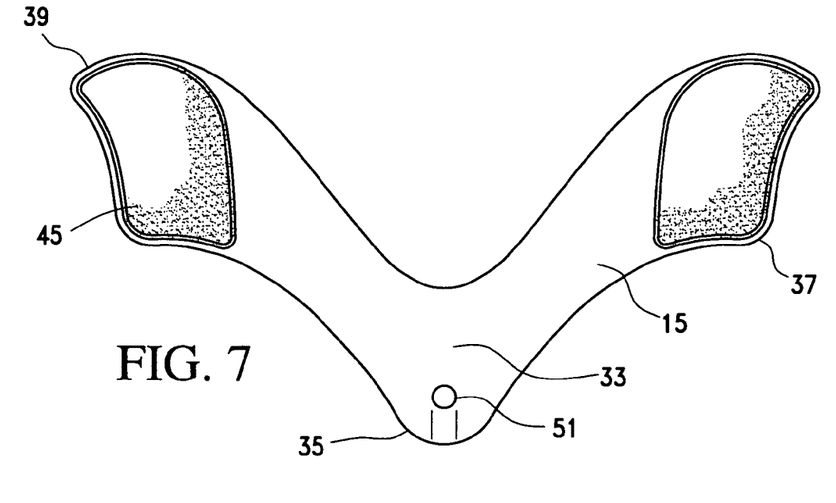
FIG. 7 is front elevational view of a precut and non-customized upper frame member of the embodiment of FIG. 1.

FIGS. 5-7 show a precut version of a knee brace, wherein lower frame member 13 and upper frame member 15 are substantially flat with the hinge 17 being preformed and protruding from the remainder of the lower frame member 13. The lower and upper frame members 13, 15 may be molded and trimmed to accommodate a wearer's leg so as to form the brace to the particular wearer. The precut yet non-customized lower and upper frame members 13, 15 may be provided in a kit with suitable buckles, fasteners such as rivets, straps and tightening devices so as to allow an orthotist or other medical professional to customize the brace by themselves according to the needs of the wearer.

As illustrated in FIGS. 5 and 6, the lower frame member 13 includes the first and second lower arms 27, 29 which continue to the lower neck 23 having the hinge 17, and the lower branch 25 having the first aperture 49. The lower frame member 13 also includes padding 43 that is positioned and precut to correspond to the first and second lower arms 27, 29.

According to FIG. 7, the upper flame member includes the first and second upper arms 37, 39 which extend to the upper neck 33 and upper branch 35 having the second aperture 51. Suitable padding 45 is also provided so as to correspond to first and second upper arms 37, 39.

As exemplified by the first and second apertures 49, 51, the lower and upper frame members 13, 15 may be configured with suitable apertures, slots, grooves, protrusions, and rings to accommodate buckles, straps and tightening mechanisms of the type taught in U.S. application Ser. No. 11/312,514. Furthermore, the lower and upper frame members 13, 15 may be preformed to include a perforated pattern of the types that are shown in connection with FIGS. 12-16 and U.S. application Ser. No. 11/312,514.

According to one variation, the lower and upper frame members are single-body entities comprising a resin impregnated carbon fiber composite system. Since the frame members are provided as kit, it is preferred that the resin is uncured. The lower and upper frame members may also be constructed from a variety of moldable materials such as TRIAX (abs/nylon blend), polypropylene, polyethylene, nylon, aramid or glass fiber prepeg with thermosetting or thermoplastic resins, and rigid foam from EVA, platezote or polyurethane.

The frame members according to the knee brace described herein may be formed to be substantially rigid, or alternatively may be flexible. For example, in the case of the frame members being flexible, they are preferably structurally flexible so as to extend closely about the leg of the wearer, yet sufficiently strong to redistribute the weight on the knee to the legs of the wearer. Of course, any frame member construction may also be used that is consistent with the frame member construction taught in U.S. application Ser. No. 11/312,514.

Figure 8:
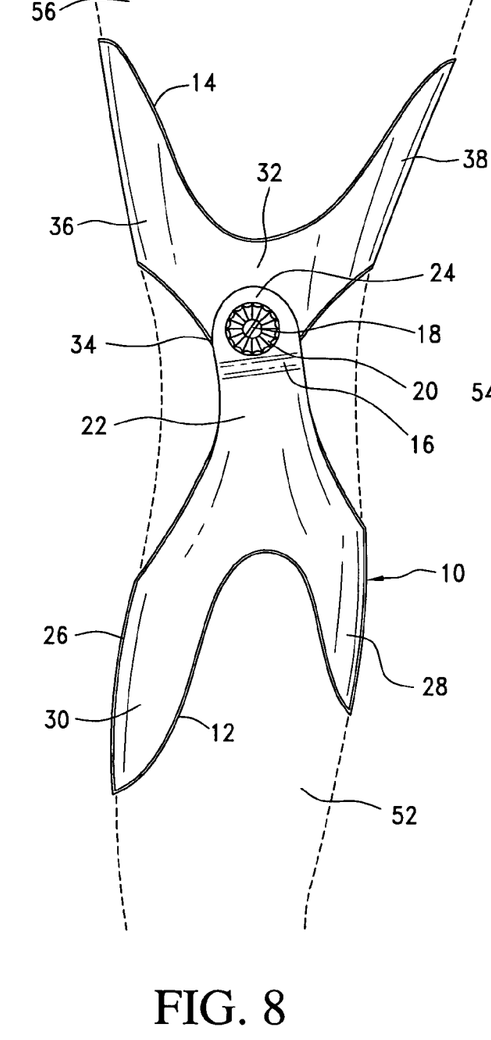
FIG. 8 is rear schematic elevational view of a variation of the embodiment of FIG. 1 placed on a leg of a wearer.

FIG. 8 illustrates a variation of the brace located on a leg. According to this embodiment, the first arm 28 is longer than the second arm 26 wherein the first arm 26 corresponds to a medial side of the lower leg portion 52 and the second arm 28 corresponds to a lateral side of the lower leg portion 52. Of course, it will be understood that one skilled in the art may modify the sizes and proportions of the lower and upper frame members 12, 14, and portions thereof beyond that which is shown herein as exemplified by the variation of FIG. 10.

Figure 9:
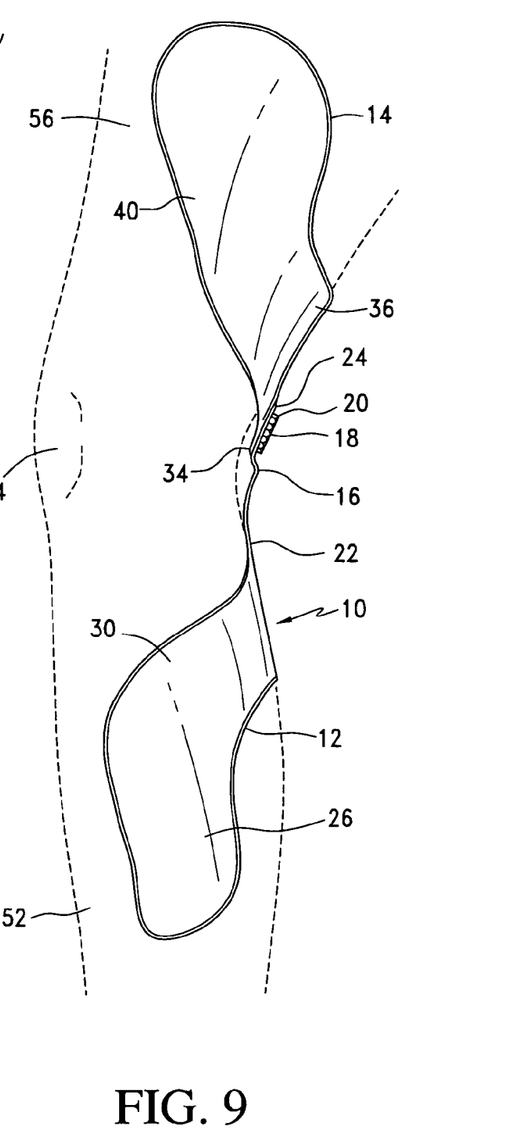
FIG. 9 is a side schematic elevational view of the embodiment of FIG. 1 placed on a leg of a wearer in a bent configuration.

As exemplified FIG. 9, the brace 10 of FIGS. 1-6 is shown on a leg wherein the upper leg portion 56 bends at the knee portion 54 relative to the lower leg portion 52. The hinge 16 is flexed at generally the same location as the knee portion 54 is bent. Due to the resiliency of the hinge, the leg is urged into a generally straight configuration when the leg is bent. As with other embodiments described herein, the hinge 16 assists the wearer in controlling the movement of the leg and knee, and especially controls their motion so to return to the leg to a straight configuration, as exemplified in FIG. 4.

Figures 10, 11:
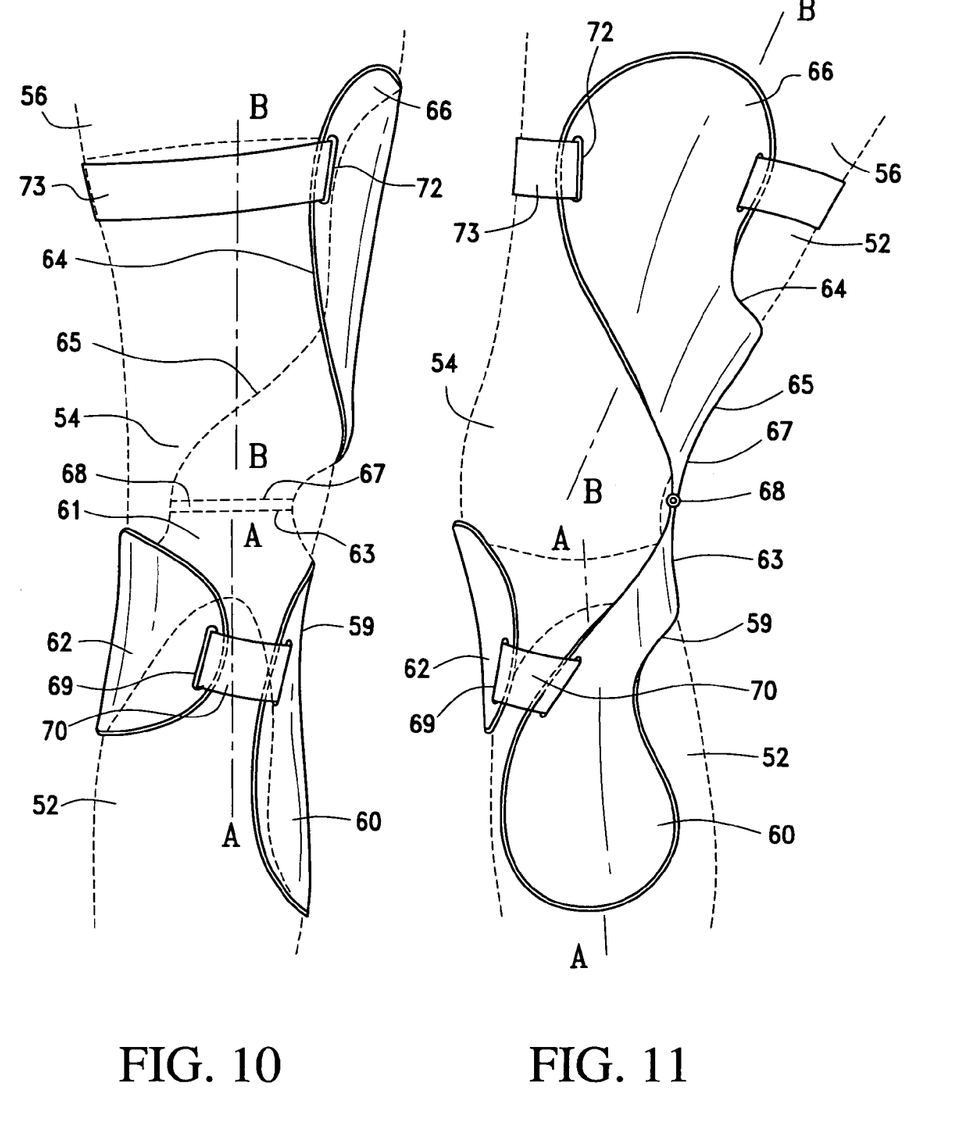
FIG. 10 is a front schematic elevational view of another embodiment of a knee brace having a posterior hinge device placed on a leg of a wearer.
FIG. 11 is a side schematic elevational view of the embodiment of FIG. 10 placed on a leg of a wearer in a bent configuration.
Figure 12:
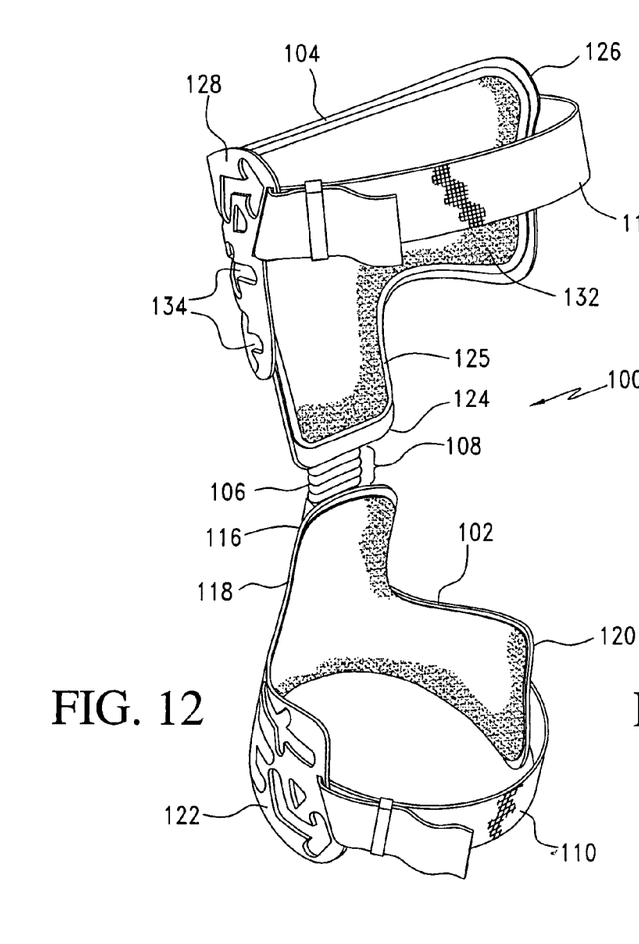
FIG. 12 is a perspective view of another embodiment of a knee brace having a posterior hinge device in a bent configuration.
Figure 13:
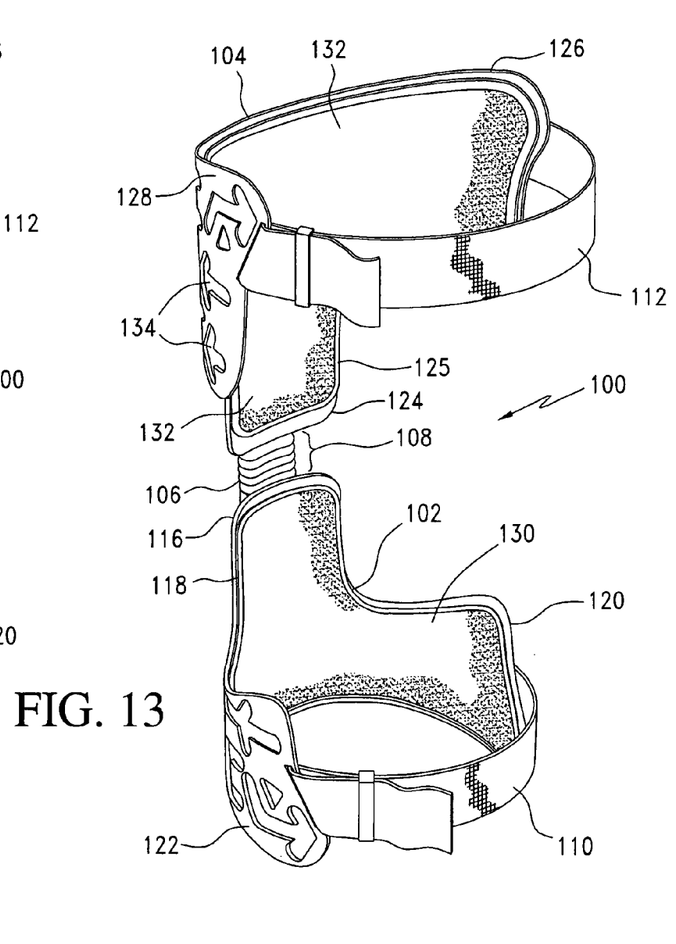
FIG. 13 is a perspective view of the embodiment of FIG. 12 in a straight configuration.
Figures 14, 15:
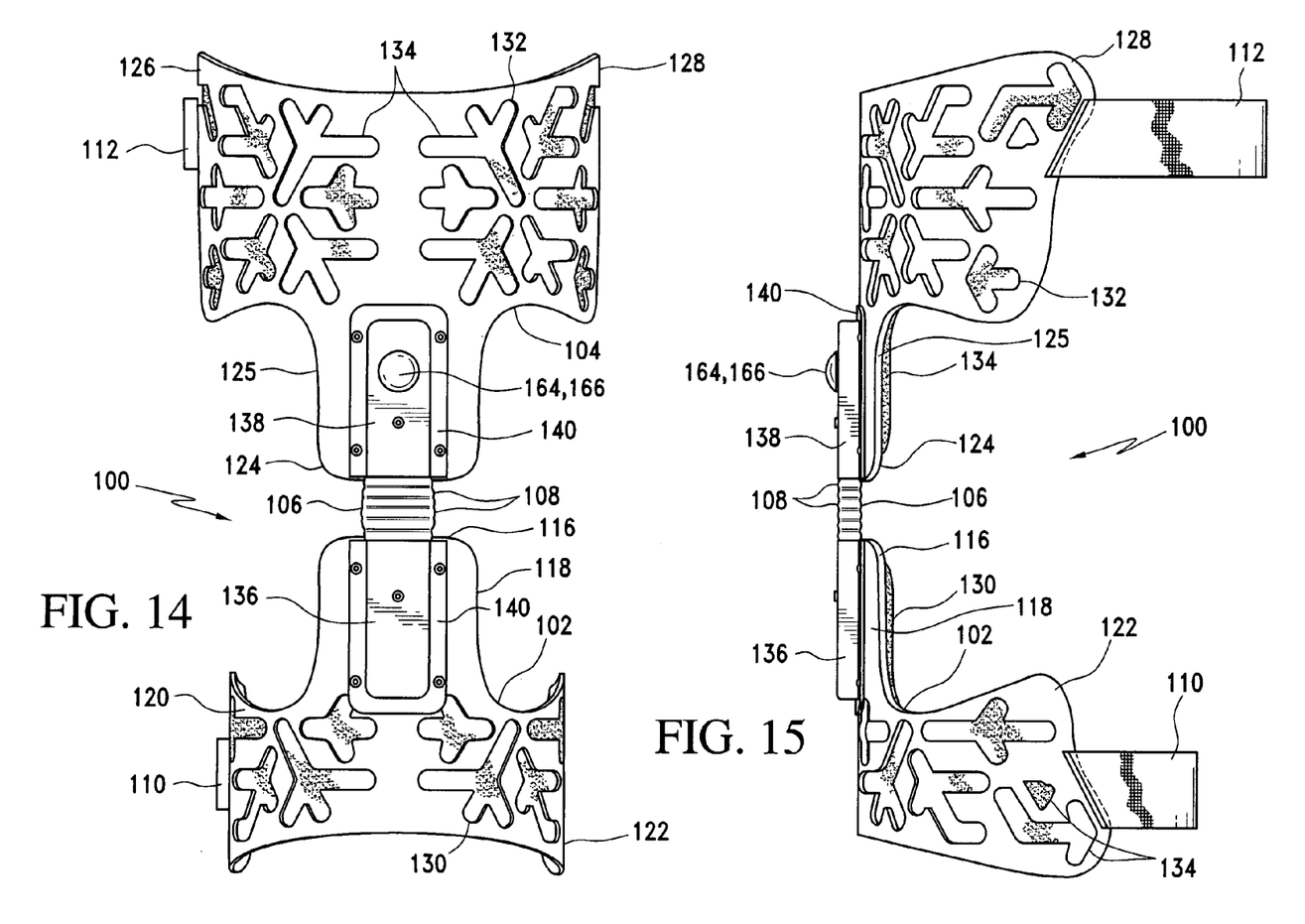
FIG. 14 is a rear elevational view of the embodiment and configuration of FIG. 13.
FIG. 15 is a side elevational view of the embodiment and configuration of FIG. 13.

FIGS. 10 and 11 show another embodiment of the knee brace wherein the first arm 60 of the lower frame member 59 generally curves along and about the axis A-A of the lower frame member and wraps about the anterior side of the lower leg 52. The second arm 62 of the lower frame member 59 only curves about the axis A-A so as to extend substantially transversely from the central portion 59. The upper frame member 64 only includes one arm that is defined by a central section 65 and a second end section 66 extending from the central section 65. The second end section 66 extends around an intended upper leg portion 56 to at least a part of the anterior side of the upper leg portion 56.

A hinge 68 connects first end portions 63, 67 of the lower and upper frame members 59, 64, respectively. According to a variation, the hinge 68 is essentially a spring device, such as in a double torsion or spiral spring or springs, connecting the lower and upper frame members 59, 64. In another variation, the lower frame member 59 may be configured to have a hinge so as to resemble the hinge in the embodiment according to FIGS. 1-3.

In variations, the hinge may be separate from the lower and upper frame members 59, 65, or may be formed by a combination of both the first end portions 63, 67 of the lower and upper frame members such that the lower and upper frame members run continuously with one another with the except of a formed hinge having at least one undulation.

FIGS. 12-18 exemplify another embodiment of a knee brace 100 according to the invention. According to this brace 100, upper and lower frame members 102, 104 are coupled by a hinge device 106. The first or lower frame member 102 defines front or anterior, and rear or posterior surfaces, and includes a first end portion 116, a central portion 118, and a second end portion defined by first and second arms 120, 122 branching from the central portion 118. The second or upper frame member 104 has front or anterior, and rear or posterior surfaces, and includes a first end portion 124, a central portion 125, and a second end portion defined by first and second arms 126, 128 that branch from the central portion 125.

As with previous embodiments, the brace 100 includes suitable padding 130, 132 corresponding to the lower and upper frame members. The padding 130, 132 preferably includes a frictional feature 133, such as a silicone coating. Similarly, as with previous embodiments, straps 110, 112 are provided which span the first and second sides of the lower and upper frame members which secure the brace onto the leg of the wearer. Taken together, the frictional feature 133 and the straps 110, 112 maintain the brace 100 from rotating and migrating on a leg of the wearer.

The brace 100 has upper and lower brackets 136, 138 which are secured to and combine with the lower and upper frame members 102, 104, respectively, to define channels therewith. As will be discussed more fully in connection with FIGS. 16-18, these channels 136, 138 receive portions of the hinge device 106.

According to this embodiment, the hinge device 106 includes a cover 108 located between the upper and lower brackets 136, 138, and a locking mechanism 164 having a lock 170 with a cover 166 which allows for selective activation of the hinge device 106. The lock 170 preferably protrudes through and from the upper bracket 138. The brackets 136, 138 have flanges 140 which are secured to the lower and upper frame members 102, 104 so as to prevent interference with the portions of the hinge device 106 located in the channels.

Preferably, when the locking mechanism 164 is activated or in a locked configuration, the hinge device 106 restrains movement of the upper frame member 104 relative to the lower frame member 102 within a preferable range of 10°-30°. However, the brace may be configured for any desirable range useful to the wearer of the brace. Moreover, the brace may be configured so that the hinge device provides resistance, as in the aforementioned embodiments, even when the hinge device 106 is not locked.

This particular embodiment is useful for skiers since the brace reduces or eliminates the load of the skier off of the knee and the quadriceps when skiing. When a skier is ready to go down a ski slope, he pushes the button on the locking mechanism and the brace locks the upper frame member relative to the lower frame member within a given range of angles. It follows that when the skier is finished with skiing, the locking mechanism is released and the upper frame member is able to move freely relative to the lower frame member thereby permitting the wearer a freedom of motion of approximately 0°-140°.

Adjustable straps 110, 112 are secured to the first and second arms of the lower and upper frame members 102, 104 for securing the brace 100 against the leg of a wearer. These straps 110, 112 may be secured to the first and second arms by extending through slots (not shown) defined by the first and second arms. In other variations, the straps 110, 112 may be secured to the lower and upper frame members with fasteners or other suitable securing means. The straps may be either elastic or substantially inelastic. Exemplary variations of the straps and means for securing the straps are found in U.S. application Ser. No. 11/312,514.

The lower and upper frame members 102, 104 have a ventilated structure 134 defined by a plurality of apertures or slots. The ventilated structure 134 provides a transfer of air through portions of the lower and upper frame members 102, 104, and greatly reduces the heat that may arise between the brace and a wearer's skin. Exemplary variations of the lower and upper frame members and their structure may be adapted in any of the manners described in connection with the shells of U.S. application Ser. No. 11/312,514.

The ventilated structure also allows for the lower and upper frame members to be sized larger than other frame elements, such as the lower and upper frame members in the embodiment of FIG. 1. By sizing the lower and upper frame members larger, there is a greater distribution of pressure of the lower and upper frame members against a wearer's leg, and as such, the brace has greater comfortability to a wearer of the brace. Because there is greater surface area, and particularly taken in combination with a frictional feature of the padding, there is less likelihood that the lower and upper frame members will rotate about a wearer's leg.

While shown as being defined as a plurality of apertures extending through the lower and upper frame members, the ventilated structure may assume any one of numerous configurations that permit a transfer of air through and across the thickness of the lower and upper frame members between the first and second surfaces. In one variation, the ventilated structure comprises a plurality of elongate slots extending in parallel directions. In other variations, the ventilated structure may assume the configuration of large holes or any appropriate shape including but not limited to circles, rectangles, straight or curved lines. Moreover, certain areas of the lower and upper frame members may have regions with greater ventilation than at other areas.

The padding 130, 132 is secured on the second surfaces of the lower and upper frame members 102, 104, respectively. The padding 130, 132 cooperates with the ventilated structure 134 of the lower and upper frame members, and is preferably ventilated with a perforated structure 135. The frictional feature 133 of the padding is preferably a silicone composition that is coated on the anterior side of the perforated structure 135 without occluding the perforated structure. The padding 130, 132 includes an edging 131 which bounds the padding, which may be coated with the silicone composition. Likewise, the posterior side of the padding may be coated with the silicone composition without occluding the perforated structure.

The padding 130, 132 extends over nearly the entire second surface of the lower and upper frame members. In other variations, the padding may extend in only certain sections of the lower and upper frame members, as shown in connection with the embodiment of FIGS. 1-3. The padding may have substantially the same structure as the padding feature 42, 44 described above in reference to the embodiment of FIG. 1, and further described in U.S. application Ser. No. 11/312,514.

The padding may be secured to the lower and upper frame members in a variety of different manners readily understood by one skilled in the art. Such manners include using hook and loop fastening means, snaps or bonding with an adhesive.

Figure 16:
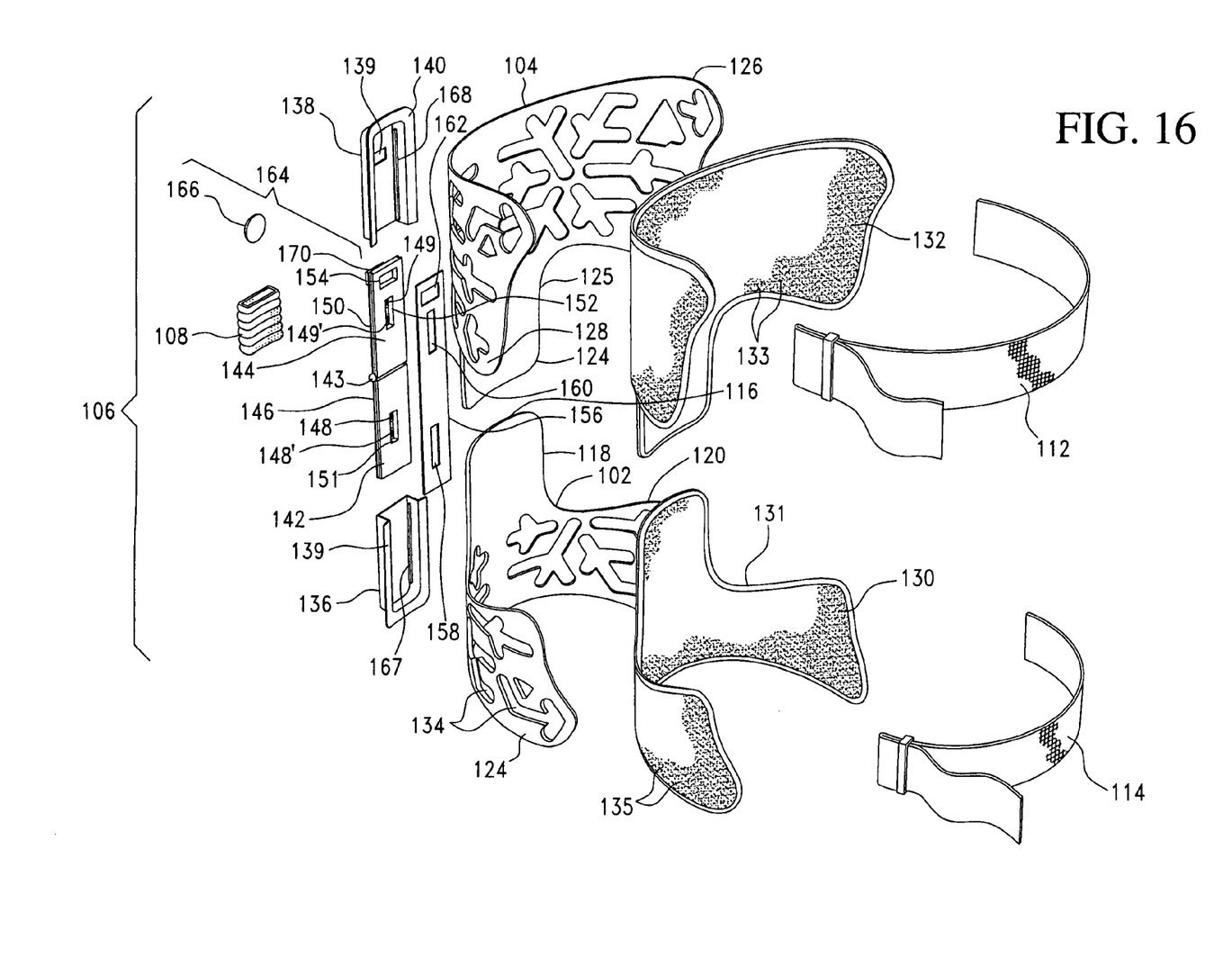
FIG. 16 is an exploded perspective view of the embodiment of FIG. 13.
Figure 17:
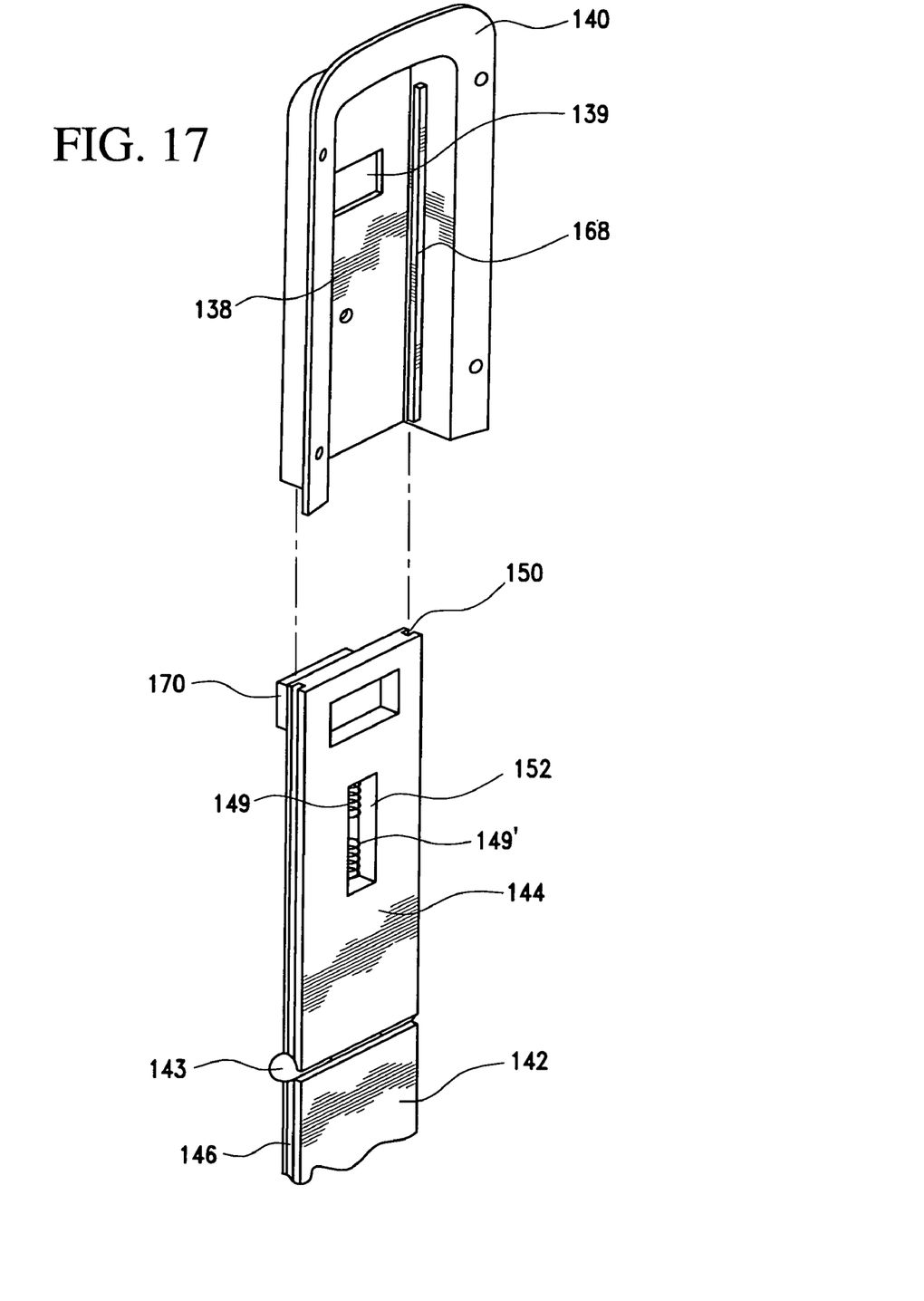
FIG. 17 is a sectional view of the hinge and bracket of FIG. 16.
Figure 18:
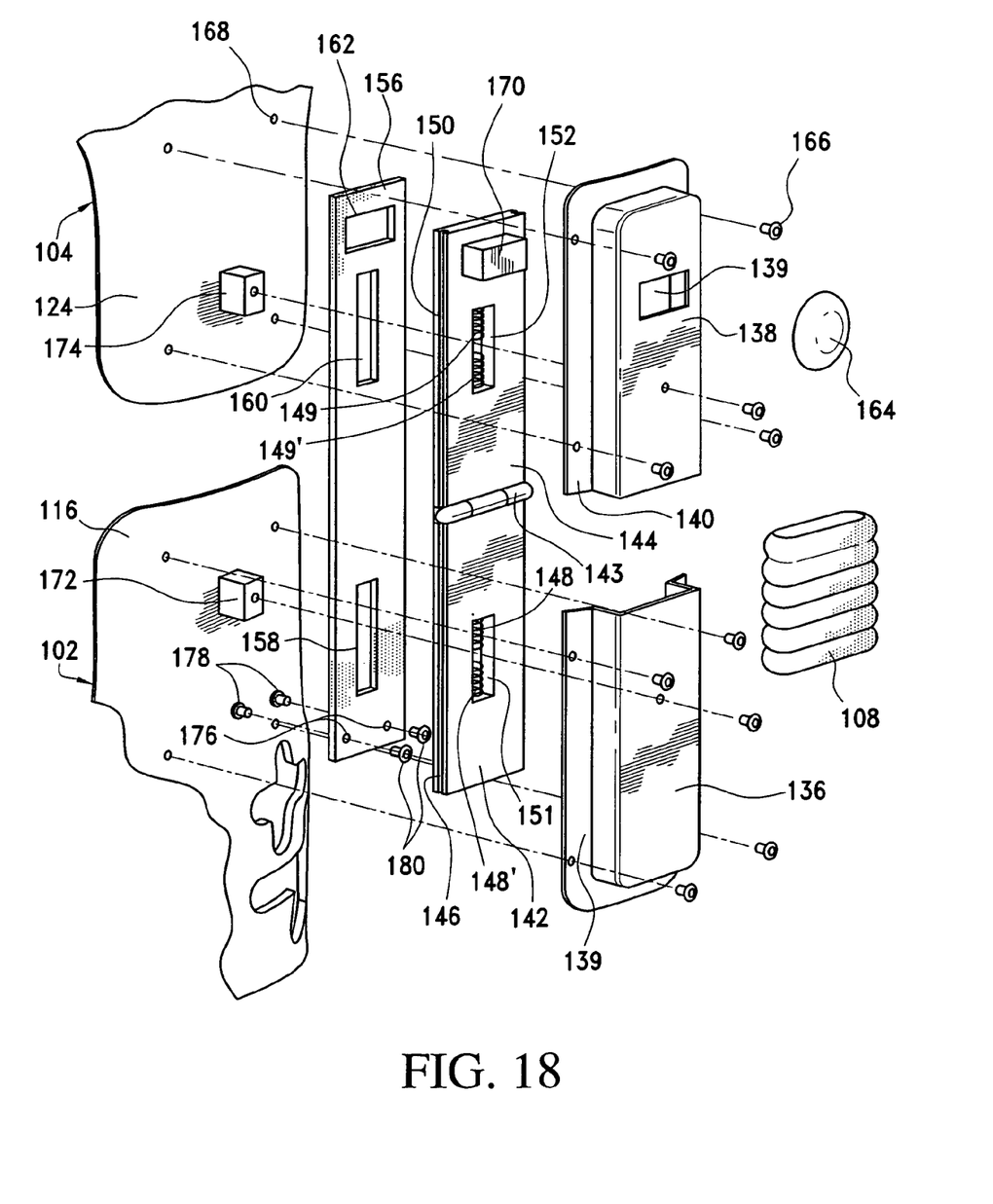
FIG. 18 is another sectional perspective view of the hinge and bracket of FIG. 17.

As best illustrated in FIGS. 16-18, the hinge device 106 comprises a hinge defined by lower and upper hinge elements 142, 144 connected to one another with a pivotable joint 143. The lower and upper hinge elements 142, 144 cooperate with a cantilever spring 156 that restrains movement of the lower and upper hinge elements 142, 144 so that they are generally pivotable relative to each other thereby enabling them to pivot from a parallel and axially aligned position towards a direction away from the lower and upper frame members 102, 104. The lock 170 is provided to permit the upper hinge element 144 to be selectively engaged with the cantilever spring 156 so as to restrain movement of the hinge elements 142, 144. The cover 108 surrounds portions of the hinge device 106 that extend between the upper and lower brackets 136, 138.

Both lower and upper hinge elements 142, 144 include elongate slots 151, 152 wherein top and bottom springs 148, 148', and 149, 149' are located, respectively. The slots 151, 152 are generally longitudinal in nature and extend along the axis of the lower and upper hinge elements 142, 144.

The upper hinge element 144 also includes an opening 154 which is configured for receiving the lock 170. The lock 170 is arranged to be pressed through the opening 154 so to protrude towards the posterior side of the upper frame member 104. When the lock 170 is not in a locked position, it is arranged to protrude from the opening 139 of the upper bracket 138, and the lower and upper hinge elements 142, 144 can slide freely relative to the cantilever spring 156.

The lock 170 can be any lockable and releasable device that is configured be pressed so as to engage the cantilever spring 156, and released so as to disengage the cantilever spring 156. The lock 170 may be spring biased, and have detents and catches which enable it to retain its position when pressed but release when it is pressed again.

As best depicted in FIGS. 16 and 17, the lower and upper hinge elements 142, 144 include longitudinal grooves 146, 150 which are located along the edges of the lower and upper hinge elements 142, 144. These grooves 146, 150 are configured for engaging ribs 167 and 168 located along the inner walls of the lower and upper brackets 136, 138. The groove and rib combination restrains movement of the lower and upper hinge elements so that they are constrained to travel linearly relative to the lower and upper frame members 102, 104.

As mentioned above, the cantilever spring 156 is arranged for cooperating and selectively locking with the lock 170. The cantilever spring 156 includes lower and upper longitudinal slots 158, 160 that correspond with the elongate slots 151, 152 of the lower and upper hinge elements 142, 144. The cantilever spring 156 also includes an opening 162 that is configured for permitting the lock 170 to engage therewith so as to effectively lock the cantilever spring 156 with the upper hinge element 144.

As exemplified in FIG. 18, the cantilever spring 156 is secured to the lower frame member 102 via fasteners 180 which extend through lower apertures 176 and engage with nubs 178 extending from the lower frame member 102. By securing the lower end of the cantilever spring 156, and leaving the upper end of the cantilever spring 156 unattached to the upper frame member 104, the cantilever spring 156 provides resistance to flexure of the brace when the locking mechanism engages the upper hinge element 144 with the cantilever spring 156.

The lower and upper frame members 102, 104 each include protrusions 172, 174, respectively, that are arranged to extend through the slots 158, 160 of the cantilever spring 156, and the slots 151, 152 of the lower and upper hinge elements 142, 144. The protrusions 172, 174 are positioned within the slots 151, 152, between springs 148, 148' and 149, 149', respectively. The springs 148, 148' and 149, 149' provide some energy return and assist in placing the hinge device 106 in a neutral position, resulting in the hinge device being substantially straight.

In view of the elongate slot 160 of the cantilever spring 156, the cantilever spring 156 is able to slide relative to the protrusion 174, when the cantilever spring 156 is not engaged with the locking mechanism 170. Similarly, the lower and upper hinge elements 142, 144, are able to slide relative to the lower and upper brackets 136, 138, due to the slots 151, 152, when the locking mechanism 170 does not engage the cantilever spring 156.

The protrusions 172, 174 limit the travel of the cantilever spring 156, and lower and upper hinge elements 142, 144, thereby limiting the rotation of the upper frame member 104 relative to the lower frame member 102.

As mentioned above, then the locking mechanism 170 engages the cantilever spring 156, the lower and upper frame members 102, 104 are only able to pivot relative to one another from a range of 10°-30°. Of course, the cantilever spring may be modified so as to permit flexion at a plurality of angles that may be desired.

The cantilever spring 156 may define different profiles from the flat profile shown herein, and is preferably constructed from a resin impregnated carbon fiber composite system that provides some flexure. The cantilever spring may also be constructed from a variety of materials providing some flexure such as TRIAX (abs/nylon blend), polypropylene, polyethylene, nylon, aramid or glass fiber prepeg with thermosetting or thermoplastic resins, and combinations thereof. Furthermore, the cantilever spring may be constructed with memory shape alloys, or have memory shape alloy wires embedded in a polymeric or composite system, that permit repeated flexure of the hinge device.

The cantilever spring may define varying degrees of stiffness, such that the central portion is generally more flexible than at end portions, or in the alternative one end portion may have greater flexibility than the other end portion.

Figure 19:
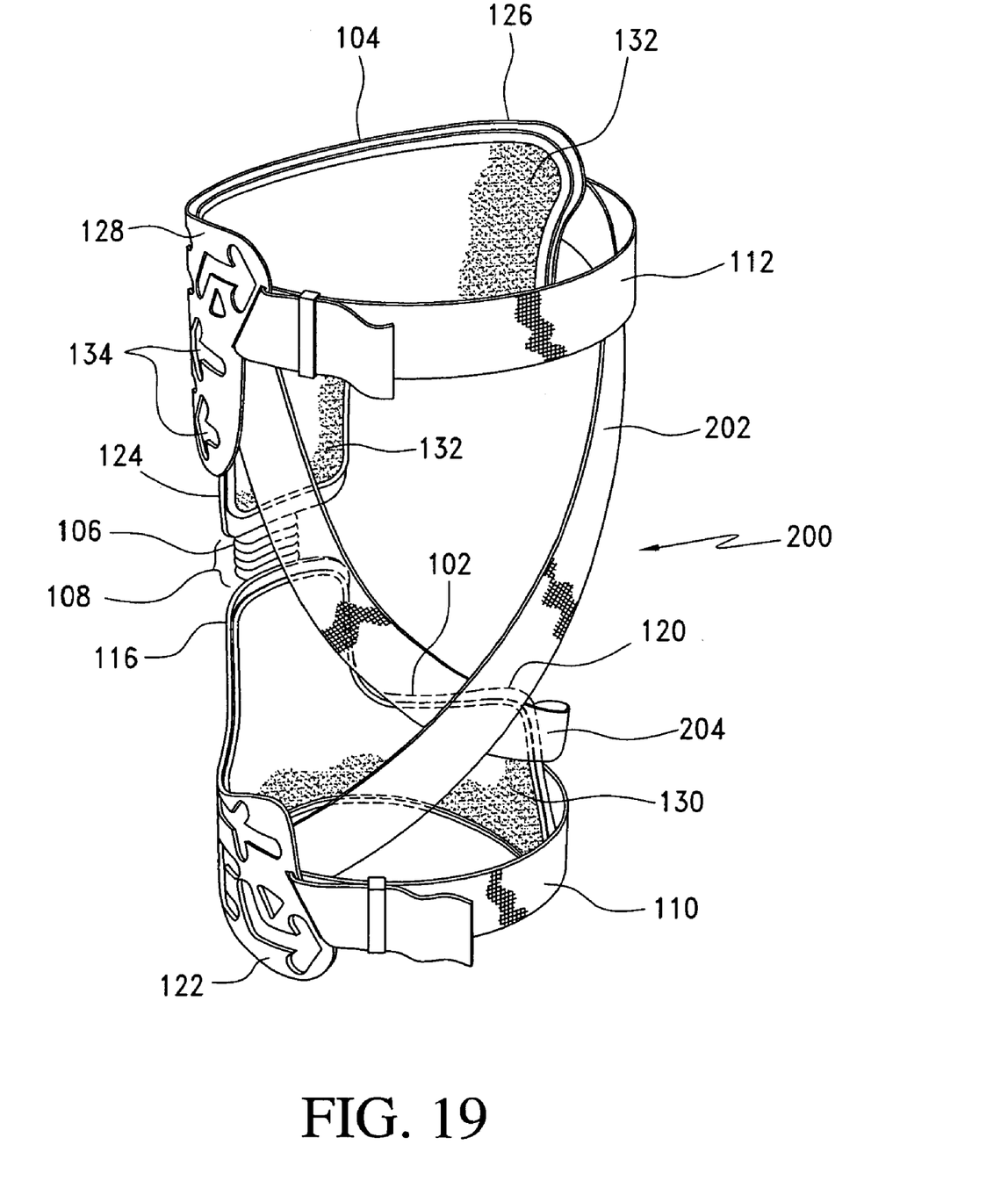
FIG. 19 is a perspective view of another embodiment of a knee brace having a posterior hinge device.

Turning to FIG. 19, another embodiment of the knee brace 200 having a similar construction to the embodiment of FIGS. 14-18 or any other of the embodiments herein, may include force straps 202, 204 which cross below the knee of the intended wearer, and apply a force along the side of the wearer's knee. The force straps may be adjusted to provide differing degrees of force against the knee.

In variations, the force straps may be configured to cross above the knee, or along one of the sides of the knee. The force straps may be configured in any manner consistent with the force straps described in U.S. application Ser. No. 11/312,514 for correcting alignment of a knee, or providing stabilization of a knee due to impact.

In any one of the embodiments described herein, sensing systems for monitoring and controlling gait dynamics may be used for the purposes of alignment, safety, and other needs of the wearer. Exemplary sensing systems that may be used with any of the embodiments herein are found in co-pending U.S. application Ser. Nos. 11/184,011 and 11/430,076 incorporated herein by reference. In addition to the hinge devices described herein, mechanical and fluid based devices may be used in substitution or in combination with the hinge devices to control braking of the hinge devices. An exemplary method for controlling braking of the knee is found in co-pending U.S. application Ser. No. 11/417,460 incorporated herein by reference.

While the foregoing embodiments have been described and shown, it is understood that alternatives and modifications of these embodiments, such as those suggested by others, may be made to fall within the scope of the invention.

The invention claimed is:

1. A knee brace having anterior and posterior sides divided by an anterior-posterior plane, and lateral and medial sides divided by a lateral-medial plane generally perpendicular to the anterior-posterior plane, the brace adapted for placement over a posterior side of a leg of a wearer of the brace, the brace comprising:

a first posterior frame member having front and rear surfaces, and including a first end portion, a central portion connecting to the first end portion, and a second end portion defined by at least one arm branching from the central portion, the first frame member central portion and first end portion arranged to align with a wearer's tibia along the lateral-medial plane thereof on the posterior side of a wearer's leg;

a second posterior frame member connected to the first frame member, the second frame member having front and rear surfaces, and including a first end portion connected to the first end portion of the first frame member, a central portion connecting to the first end portion, and a second end portion defined by at least one arm branching from the central portion, the second frame member central portion arranged to align with a wearer's femur along the lateral-medial plane thereof on the posterior side of a wearer's leg; and a posterior resilient hinge connecting the first and second frame members, and located at or near the first end portion of the first frame member, the hinge bendable across its length while accommodating movement of the knee and arranged to urge the first and second frame members into a predetermined alignment by resisting flexion of a knee, the hinge arranged to correspond to a wearer's posterior side of a knee and align along the lateral-medial plane thereof, the hinge itself formed separately and removable from the first and second frame members, an entire length of the hinge being substantially parallel to the first end portions of the first and second frame members and substantially aligned in length to the leg of the wearer when the brace is in an upright position.

2. The knee brace according to claim 1, wherein the first frame member has first and second arms each defining a curved portion located at or near the second end of the first frame member and about a central longitudinal axis of the first frame member, and extending at least laterally from the central axis.

3. The knee brace according to claim 1, further comprising an adjustment mechanism connecting and orienting the first and second frame members relative to one another.

4. The knee brace according to claim 1, further comprising a gauge providing indicia indicating a rotational position of the first frame member relative to the second frame member.

5. The knee brace according to claim 1, wherein the first and second frame members are configured for placement on a human leg such that the arms of the first and second frame members are curved so as to extend around from the posterior side to the anterior side of a leg.

6. A knee brace having anterior and posterior sides divided by an anterior-posterior plane, and lateral and medial sides divided by a lateral-medial plane generally perpendicular to the anterior-posterior plane, the brace adapted for placement over at least a posterior side of a leg of a wearer of the brace, the brace comprising:
a first posterior frame member having front and rear surfaces, and including a first end portion, a central portion connecting to the first end portion, and a second end portion having at least one arm branching from the central portion and about a central longitudinal axis, the first frame member central portion and first end portion arranged to align with a wearer's tibia along the lateral-medial plane thereof on the posterior side of a wearer's leg;
a second posterior frame member having front and rear surfaces, and including a first end portion joined to the first end portion of the first member, a central portion connecting to the first end portion, and a second end portion having at least one arm branching from the central portion, the second frame member central portion arranged to align with a wearer's femur along the lateral-medial plane thereof on the posterior side of a wearer's leg; and
a hinge device connecting the first and second frame members relative to one another, the hinge device arranged for selectively locking the second frame member at an angle relative to the first frame member, and permitting rotation of the second frame member relative to the first frame member within a predetermined range of angles, the hinge device providing resistance to flexion of knee as the first and second frame members rotate relative to one another, the hinge device arranged to correspond to a wearer's posterior side of a knee and align along the lateral-medial plane thereof;
wherein the hinge device includes a resilient cantilever spring secured to the first frame member;
wherein the hinge device further includes lower and upper hinge elements connected to one another via a joint, the upper hinge element selectively engageable with the cantilever spring;
wherein the first and second frame members include protrusions extending from the rear surface thereof, the protrusions extending through corresponding elongate slots defined by the cantilever spring, and the lower and upper hinge elements;
wherein the elongate slots of the lower and upper hinge elements include at least one spring element arranged to restrict sliding of the frame member protrusions within the elongate slots.

7. The knee brace according to claim 6, wherein the hinge device includes a locking mechanism supported by the upper hinge element that is configured to selectively secure the cantilever spring relative to the upper hinge element thereby positioning the upper frame member relative to the lower frame member at a predetermined angle.

8. The knee brace according to claim 6, wherein the hinge device includes lower and upper brackets connecting to the first and second frame members respectively, and forming channels therewith for receiving end portions of the cantilever spring and the lower and upper hinge elements.

9. The knee brace according to claim 8, wherein the lower and upper hinge elements include elongate grooves defined along edges thereof for receiving ribs defined along interior surfaces of the lower and upper brackets thereby permitting the lower and upper hinge elements to slide linearly relative to the lower and upper brackets.

10. The knee brace according to claim 6, wherein the second frame member is arranged to be locked relative to the first frame member within the predetermined range of 5° to 30°, the hinge device permitting rotation of the second frame member relative to the first frame member within the predetermined range.

11. The knee brace according to claim 6, wherein the first and second frame members are configured for placement on a human leg such that the arms of the first and second frame members are curved so as to extend around from the posterior side to the anterior side of a leg.

12. A brace having anterior and posterior sides divided by an anterior-posterior plane, and lateral and medial sides divided by a lateral-medial plane perpendicular to the anterior-posterior plane, the brace adapted for placement over at least a posterior side of a leg of a wearer of the brace, the brace comprising:
a first frame member;
a second frame member;
a hinge arrangement including a first elongate arm connecting to the first frame member, a second elongate arm connecting to the second frame member, and a hinge located between and connecting the first and second arms, the first and second arms being substantially rigid, the hinge arrangement arranged to correspond to a wearer's posterior side of a knee and align along the lateral-medial plane thereof; and
an elongate resilient element being substantially straight across a point of articulation when the brace is in an upright configuration and bendable while accommodating movement of the knee as a wearer's knee goes into flexion, the resilient element located adjacent to and along a surface of the hinge arrangement so as to correspond to movement of the hinge arrangement;
wherein the resilient element has a predetermined configuration such that the resilient element urges the hinge arrangement into a predetermined configuration.

13. The brace according to claim 12, wherein the hinge arrangement includes a release device arranged to deactivate the resilient element.

14. The brace according to claim 1, wherein the hinge is formed from a polymeric material different from at least one material forming the first frame member.

15. The brace according to claim 12, wherein resilient element is formed from a polymeric material and is individually separate from the hinge arrangement.

16. A brace having anterior and posterior sides divided by an anterior-posterior plane, and lateral and medial sides divided by a lateral-medial plane forming a midline and perpendicular to the anterior-posterior plane, the brace adapted for placement over at least a posterior side of a leg of a wearer of the brace such that the midline of the brace is arranged to correspond to a lateral-medial plane aligned with a wearer's tibia and femur, the brace comprising:

- an upper frame member having first and second arms extending generally about the midline;
- a lower frame member having first and second arms extending generally about the midline; and
- upper and lower hinge elements connecting the lower and upper frame members, the upper and lower hinge elements aligned along the midline and located on the posterior side of the brace along a posterior side of a wearer's leg and following a lateral-medial plane of the wearer's leg, the upper and lower hinge elements corresponding to at least a portion of a wearer's tibia and femur, respectively, the upper and lower hinge elements connecting at a middle section corresponding at least to the wearer's knee and having a predetermined shape configuration which is bendable, sections of the upper and lower hinge elements outside of the middle section are substantially rigid;
- a resilient element aligning to the lateral-medial plane of a wearer's knee, the resilient element having a predetermined shape configuration across its entire length including a surface located adjacent to at least the middle section, the predetermined configuration of the middle section and the adjacent surface of the resilient element being the same;
- wherein the middle section freely articulates and the resilient element itself bends and resists articulation of the middle section while still permitting articulation of the middle section, the resilient element urging the middle section into its predetermined configuration thereby resisting flexion of a wearer's knee.

* * * * *